United States Patent [19]

Takasaki

[11] Patent Number: 4,925,795

[45] Date of Patent: May 15, 1990

[54] METHOD OF USING G-4 AMYLASE TO PRODUCE HIGH MALTOTETRAOSE AND HIGH MALTOSE CONTENT STARCH HYDROLYSATES

[75] Inventor: Yoshiyuki Takasaki, Matsudo, Japan

[73] Assignees: Agency of Industrial Science & Technology; Ministry of International Trade & Industry, both of Tokyo, Japan

[21] Appl. No.: 946,785

[22] Filed: Dec. 29, 1986

[51] Int. Cl.$^5$ .................. C12P 19/22; C12P 19/14; C12N 9/26; C12R 1/09

[52] U.S. Cl. ................................. 435/95; 435/99; 435/201; 435/835; 426/48

[58] Field of Search ............... 435/202, 210, 209, 95, 435/99, 98, 835, 22, 201; 426/28, 658, 48

[56] References Cited

U.S. PATENT DOCUMENTS 3,922,196 12/1975 Leach et al. .................. 127/29
3,998,696 12/1976 Yomoto et al. ............... 435/202

FOREIGN PATENT DOCUMENTS 60-227676 11/1985 Japan.

*Primary Examiner*—Elizabeth C. Weimar
*Attorney, Agent, or Firm*—Oblon, Spivak, McClelland, Maier & Neustadt

[57] ABSTRACT

Maltotetraose or maltose is specifically produced in a high yield from starch by causing an amylase produced by a microorganism of genus *Bacillus circulans* G-4 to act on the starch.

4 Claims, 1 Drawing Sheet

METHOD OF USING G-4 AMYLASE TO PRODUCE HIGH MALTOTETRAOSE AND HIGH MALTOSE CONTENT STARCH HYDROLYSATES

BACKGROUND OF THE INVENTION

This invention relates to a novel amylase produced by a microorganism belonging to the genus Bacillus and to a method for the production of maltotetraose from starch using the amylase.

DISCUSSION OF THE BACKGROUND

It is known that glucoamylase (which is capable of hydrolyzing starch into glucose) and that β-amylase and α-amylase (which are capable of hydrolyzing starch into maltose) are widely present in nature. Amylases of still larger molecular weights which are severed by such oligosaccharide units as, for example, maltotriose (G3), maltotetraose (G4), maltopentaose (G5), and maltohexaose (G6), these oligosaccharides have been attracting interest as extenders, excipients, or flavor conditioners for foodstuffs. Particularly the G4 through G7 oligosaccharides have been attracting interest as substrates for diagnostic determination of amylase activities. In spite of such interest, however, very few reports of successful production of these oligosaccharides have been published. It has been known in the art that the amylase which is produced by *Pseudomonas stuzeri* hydrolyzes amylose and amylopectin in maltotetraose units from their non-reducing terminals.

It is reported, however, that this enzyme leaves behind a macromolecular limit dextrin after hydrolysis of amylopectin or glycogen (Archive Biochemistry and Biophysics, Vol. 145, pages 105–114 (1971)). It is reported that the yield of maltotetraose from starch by the use of this enzyme is about 55% (U.S. Pat. No. 3,654,082).

SUMMARY OF THE INVENTION

An object of this invention is to provide an amylase capable of producing maltotetraose in very high yields of about 65 to 75% from starch.

Another object of this invention is to provide a method for the production of maltotetraose in a high yield from starch by the use of the amylase mentioned above.

To attain the objects described above, this invention effects the production of maltotetraose in a yield of 65 to 75% from starch by causing an amylase which is produced by a microorganism belonging to genus Bacillus to act upon the starch.

The production by the use of this amylase is economical because this amylase, when allowed to act on starch, produces maltotetraose in a high yield while leaving behind virtually no limited dextrin of a high molecular weight.

The above and other objects and features of the invention will become more apparent from the following detailed description with reference to the accompanying figures.

DETAILED DESCRIPTION OF THE PREFERRED EMBODIMENTS

The inventor made an extensive search for microorganisms in nature with a view to establishing a method for the production of oligosaccharides. He has consequently found that a novel amylase capable of hydrolyzing such α-glucans as amylose, amylopectin, and starch specifically into maltotetraose (G4) is produced by a microorganism identified as *Bacillus circulans*. It has been confirmed that the amylase produced by this microorganism belonging to genus Bacillus produces maltotetraose in an extremely high yield of about 65 to 75% from starch. The yield of the maltotetraose produced from starch is affected by the particular kind of starch used, the degree of dextrinization (DE), the amount of enzyme used, etc. Generally, 1 to 5% of glucose (G1), 5 to 15% of maltose (G2), 5 to 15% of maltotriose, 65 to 75% of maltotetraose, 1 to 5% of maltopentaose, and 1 to 15% of other saccharides are produced.

When potato starch of DE 4.2 is used, for example, the composition of sugars produced is as shown in Table 1.

It is noted from this table that this amylase, when allowed to act on starch, produces maltotetraose in a very high yield while leaving behind virtually no limit dextrin of a high molecular weight.

TABLE 1

| Sugar produced | Content |
| --- | --- |
| G1 | 2.9 (%) |
| G2 | 9.2 |
| G3 | 10.4 |
| G4 | 73.9 |
| G5 | 1.7 |
| G6 ~ | 1.9 |

From these results, it is logical to conclude that this amylase is an enzyme which possesses a notably different substratal specificity from the amylase produced by *Pseudomonas stuzeri*. Besides, this amylase is recognized to have an optimum pH extending over a wide range and a small molecular weight as compared with the amylase of *Pseudomonas stuzeri* (Archive Biochemistry and Biophysics, Vol. 145, page 105 (1971)), indicating that this is a novel enzyme. The inventor has named this enzyme as amylase G4.

The present invention which has originated from this finding is directed to a method for the production of maltotetraose from starch by the use of the amylase G4, belonging to genus Bacillus, which method comprises causing the amylase G4, capable of producing maltotetraose as a main component, to act on starch, amylose, amylopectin, glycogen, or a partial hydrolyzate thereof.

Now, this invention will be described in detail below.

The enzyme which is produced by the present invention possesses the following enzymatic properties.

(1) Activity: This amylase hydrolyzes α-glucans such as amylose, amylopectin, and glycogen into hydrolyzates including maltotetraose as a main component. This enzyme is a species of α-amylase possessing the mode of hydrolysis of the endo-form and, when allowed to act on liquefied starch, produces maltotetraose in a yield of about 65 to 75%.

Figure 1A:
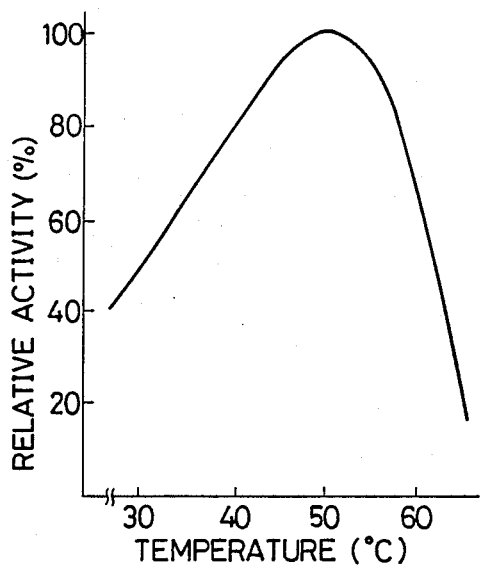
FIG. 1(a) is a graph showing the optimum temperature of amylase according to this invention.

(2) Range of working temperature and optimum temperature: In the presence of 1% soluble starch and 0.05M phosphate buffer, the amylase remains active up to about 75° C. The optimum temperature of this amylase is about 50° C. (FIG. 1(a)).

Figure 1B:
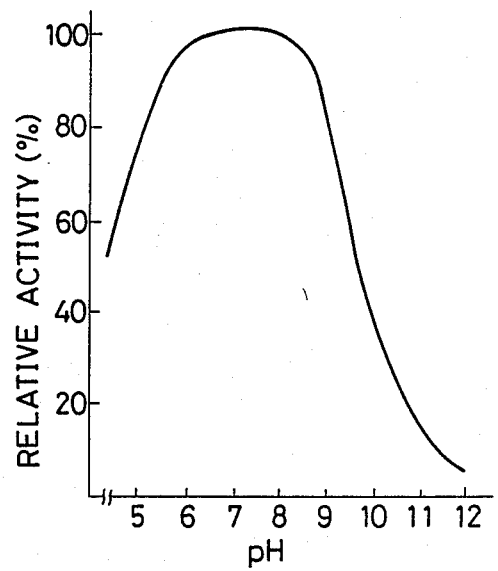
FIG. 1(b) is a graph showing the optimum pH of amylase according to this invention.

(3) Range of working pH and optimum pH: This amylase exhibits activity over a wide range of pH values from about 4 to about 12. The optimum pH is 6 to 8.5 (concerning the activity in the presence of 0.05M acetate or phosphate buffer and 1% soluble starch, FIG. 1(b)).

Figure 1C:
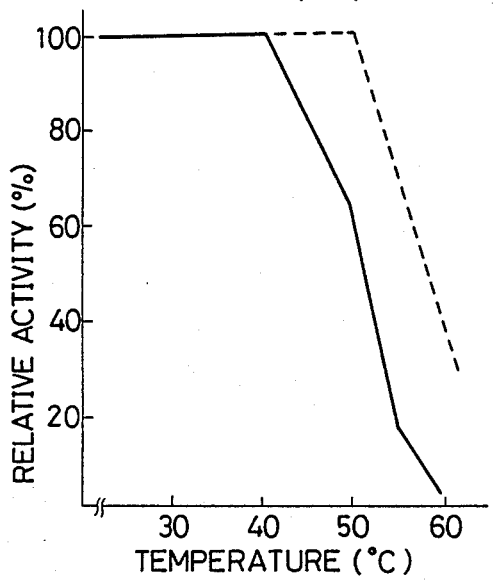
FIG. 1(c) is a graph showing thermal stability of amylase according to this invention.

(4) Thermal stability: This amylase, when heated in the presence of 0.1M Tris buffer (pH 7.0), is inactivated by about 40% after 10 minutes' heating at 50° C. and by about 85% after 10 minutes' heating at 55° C. (the continuous line in FIG. 1(c)).

Figure 1D:
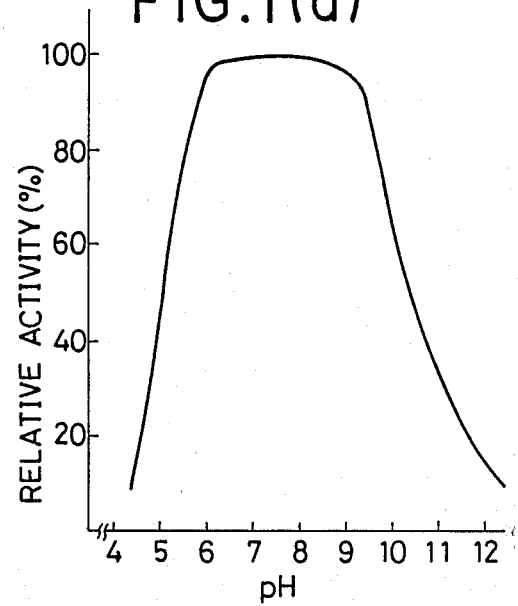
FIG. 1(d) is a graph showing the pH stability of amylase according to this invention.

(5) pH stability: When this amylase is left standing at room temperature (25° C.) in the presence of 0.1M buffer for three hours and then tested for residual activity, it is found to retain stability in a pH range of 6 to 9 (FIG. 1(d)).

(6) Stabilization: This amylase in the presence of calcium ion is recognized to exhibit enhanced thermal stability (the broken line in FIG. 1(c)).

(7) Inhibitor: This amylase is recognized to be inhibited by about 100%, about 95%, about 50%, and about 30% respectively by $HgCl_2$, $CuSO_4$, $ZnSO_4$, and $AgNO_3$ each used in a concentration of $5 \times 10^{-3}M$.

(8) Method of purification: From the centrifuged supernatant of a liquid culture broth, this amylase can be purified up to electrophoretic uniformity through fractionation with ammonium sulfate, DEAE-Sepharose column chromatography, Biogel A-0.5 m column chromatography, and rechromatography using the same gel.

(9) Molecular weight: The molecular weight of this amylase, determined by the gel filtration method using Biogel A-0.5m, is found to be about 10,000.

(10) Method for determination of enzyme activity: A suitable amount of the amylase is added to 0.5 ml of a 2% soluble starch dissolved in 0.1M phosphate buffer (pH 7.0), made up to a total volume of 1 ml with water, and incubated at 40° C. The amount of the amylase which, under the conditions mentioned above, produces a reducing power corresponding to 1$\mu$ mole of glucose in one minute is defined as 1 unit.

Comparison of the enzymatic properties of this amylase shown above with those of the maltotetraose-producing amylase of *Pseudomonas stuzeri* known to the art prior to the filing of the present invention reveals that (1) the amylase of this invention has an optimum pH over a wide range from 6 to 8.5, whereas the amylase of *Pseudomonas stuzeri* has an optimum pH near 8, that (2) the amylase of this invention produces maltotetraose in a yield of about 65 to 75% from starch, whereas the amylase from *Pseudomonas stuzeri* produces the sugar in a yield of about 55%, and that (3) the amylase of this invention has a molecular weight of about 10,000, whereas the amylase from *Pseudomonas stuzeri* has molecular weights of 48,000 and 58,000 (Biochemistry and Biophysics Acta, Vol. 566, page 88 (1979)). Thus, the amylase of this invention and that from *Pseudomonas stuzeri* are remarkably different in the yield of maltotetraose from starch, the optimum pH, and the molecular weight. As described above, therefore, this amylase can be recognized as a novel enzyme.

As a typical microorganism capable of producing the amylase of this invention, *Bacillus circulans* G-4 is cited.

The taxonomical properties of this microorganism are shown below. The *Bacillus circulans* G-4 was deposited under the Budapest Treaty at the Fermentation Research Institute, Agency of Industrial Science and Technology on June 15, 1985 and was assigned the deposit number FERM BP-820.

Taxonomical properties:
(1) Form: Rod 0.5 to 1 (width)$\times$5 to 6 (length) u, non-motile, gram-negative.
(2) Spore: Generally one spore found near terminal end, with no swollen sporangia recognized.
(3) Nutrient broth: Cloudy suspension and sedimentation observed.
(4) Nutrient agar: Satisfactory growth, light yellow to light brown, irregular contour on periphery and surface.
(5) Glucose nutrient agar: Satisfactory growth, light yellow to light brown.
(6) Glucose nitrate agar: Poor growth.
(7) Potato: Satisfactory growth in milky white.
(8) Glucose-asparagine agar: Rather poor growth, light yellow to light brown.
(9) Tyrosine-agar: Satisfactory growth, slightly brown.
(10) Milk: Slow coagulation and peptonization.
(11) Indol: Not produced.
(12) Catalase: Produced.
(13) Acetylmethyl carbinol: Not produced.
(14) Hydrogen sulfide: Not produced.
(15) Citric acid: Utilization recognized.
(16) Reduction of nitrate: Negative.
(17) NaCl broth: Satisfactory growth attained in medium containing up to 8% NaCl and slight growth attained in medium containing 10% NaCl.
(18) Utilization of carbohydrate: Acids formed from D-glucose, D-fructose, D-mannose, L-arabinose, D-ribose, maltose, sucrose, starch, etc. without evolution of gas. No satisfactory utilization of D-xylose, L-rhamnose, or L-sorbose recognized.
(19) Optimum temperature for growth: About 26° C.
(20) Maximum temperature for growth: About 60° C.
(21) Temperature for extinction: No extinction caused by 30 minutes' heating at 100° C.

On the basis of the foregoing taxonomical properties, this microorganism was identified by reference to "Bergey's Manual of Determinative Bacteriology", 7th and 8th editions, published by the Williams and Wilkins Company in 1957 and 1974, as *Bacillus circulans* and was designated as *Bacillus circulans* G-4.

The culture for the production of the amylase G4 of this invention requires use as nitrogen sources of meat extract, peptone, yeast extract, casein, corn steep liquor, soybean cake, etc., which are organic nitrogen sources generally adopted in the culture of microorganisms and as carbon sources of starch, dextrin, maltose, glucose, sucrose, etc. As supplementary nutrient sources, inorganic nitrogen sources, phosphates, magnesium salts, and various metal salts are incorporated in the medium. The culture is aerobically carried out at a pH in the range of 5 to 9 and at a temperature in the range of 20° to 60° C.

Since the amylase G4 is an enzyme produced extracellularly, the culture broth occurring at the end of the culture is filtered or centrifuged to remove the cells and recover the supernatant. The recovered supernatant, when necessary, is concentrated, salted out with ammonium sulfate or sodium sulfate or diluted with acetone, isopropanol, ethanol, or methanol to collect the enzyme as a precipitate. The collected percipitate is dried and put to storage.

The reaction for saccharification of starch by the use of the amylase G4 is carried out as follows. The starch is liquefied with an acid or an α-amylase. Since the degree of liquefaction affects the yield of maltotetraose, the starch liquefied to not more than DE 20 is desirably used ("DE value" representing the reducing power in a given solid as the glucose content in percentage). The substrate concentration is generally fixed in the range of 5 to 40%. The reaction pH is generally in the range of 5 to 9 and the reaction temperature in the range of 40° to 60° C. Since this enzyme is thermally stabilized notably in the presence of calcium ion, the medium adopted for the reaction of a saccharification is desired to incorporate therein a calcium salt in a concentration of $5 \times 10^{-4}$ to $2 \times 10^{-2}$M.

In the reaction for saccharification of such a substrate as starch, amylopectin, or glycogen which possesses an α-1,6-glucosidic linkage by the use of the amylase G4, the reaction is accelerated by the presence of such an α-1,6-glucosidase as isoamylase or pullulanase and, as a result, the amount of the amylase G4 to be used will be reduced and the yield of maltotetraose increased.

The α-1,6-glucosidases are enzymes capable of hydrolyzing the α-1,6-glucosidic linkage present as in amylopectin, glycogen, or pullulan and are produced by various bacteria, actinomycetes, and yeasts. Owing to the difference in substratal specificity, they are called isoamylase, pullulanase, etc. At times, they are collectively referred to as debranching enzymes, α-1,6-glucosidases, and so on. The amylase G4 of the present invention is enabled by any of these α-1,6-glucosidases to increase the yield of maltotetraose with high efficiency. In the case where the yield of maltotetraose obtained when the amylase G4 is used alone to act on starch as a substrate is about 65%, for example, the yield in the presence of pullulanase can be increased up to about 74%.

Although the amylase G4 is incapable of hydrolyzing the α-1,6-glucosidic linkage, it has the ability to effect regular decomposition of amylose and amylopectin with the maltotetraose units and sever the vicinity of the chain in the branch of amylopectin. Thus, it can effectively hydrolyze amylopectin or starch while leaving behind practically no limit dextrin. For this reason, when this amylase is used in combination with such a maltose-producing enzyme as β-amylase, it can produce maltose in a high yield of 70 to 80% from amylopectin or starch containing it.

Generally, as a maltose-producing enzyme, the β-amylase originating in plants such as soybean, wheat, and barley or the β-amylase produced by microorganisms of genus Bacillus (Agriculture Biological Chemistry, Vol. 40, page 1515 (1976)) is used. Besides, the maltose-producing α-amylase produced by microorganisms belonging to genus Bacillus, genus Aspergillus, and genus Streptomyces can likewise be used.

The reaction for saccharification of starch by the combined use of the amylase G4 and the maltose-producing enzyme is carried out as follows.

Generally, the starch is liquefied preparatorily with an acid or a liquefaction type α-amylase. The degree of liquefaction affects the yield of maltose in such a manner that it is desired to be as low as permissible. Generally, not more than DE 5 is used. This reaction is generally performed at a substrate concentration in the range of 5 to 40%, at a pH in the range of 5 to 8, and at a temperature in the range of 40° to 60° C. Since the amylase G4 is thermally stabilized by the presence of calcium ion, the medium used for the saccharification incorporates therein a calcium salt in a concentration generally in the range of about $5 \times 10^{-4}$ to $2 \times 10^{-2}$M.

The amylase G4 and the maltose-producing enzyme such as a β-amylase are desired to act simultaneously on the starch. Otherwise, the maltose-producing enzyme is used to start saccharification of the starch and, during the course of the reaction, the amylase G4 is added thereto to continue the reaction or the amylase G4 is first used to start the reaction and subsequently the maltose-producing enzyme is added to support the reaction.

Now, this invention will be described more specifically below with reference to working examples.

EXAMPLE 1

In a conical flask having an inner volume of 200 ml, 30 ml of a medium containing 0.3% of dipotassium phosphate, 0.1% of magnesium sulfate (heptahydrate), and 1% of soluble starch was heated at 120° C. for 10 minutes for sterilization. The Bacillus circulans G-4 (FERM-BP 820) was inoculated to the sterilized medium and subjected to shaken culture at 30° C. for 4 days.

After completion of the shaken culture, the culture broth consequently produced was centrifuged. The supernatant resulting from the centrifugation was analyzed for amylase G4 content. Thus, the culture was found to have produced 6.1 units of the amylase G4 per 1 ml of the medium.

To the aforementioned supernatant was added cold acetone of a volume twice as much as the supernatant to form a precipitate, which was dissolved in water and used as an enzyme solution of amylase G4.

EXAMPLE 2

Starch was hydrolyzed by the use of the enzyme solution obtained in Example 1. As a substrate, 100 mg (as solid) of liquefied starch of DE 4.2 which was liquefied by the use of Bacillus α-amylase was used. The substrate, with $5 \times 10^{-3}$M of calcium chloride and an amount, in the range of 0.5 to 4 units, of the amylase G4 as indicated in Table 2 added thereto, was filled up with water to total volume of 1 ml and then incubated at 50° C. for 44 hours. After completion of the reaction, the reaction solution was assayed for the maltotetraose content by high-speed liquid chromatography. The results were as shown in Table 2.

TABLE 2

| Amount of enzyme used | Maltotetraose content in hydrolyzate produced after 44 hours' reaction of saccharification |
|---|---|
| 0.5 (u/g of substrate) | 40.6 (%) |
| 1 | 57.0 |
| 2 | 64.6 |
| 3 | 67.5 |
| 4 | 72.6 |

In the hydrolyzate resulting from 44 hours' saccharification of the substrate containing 4 units of the enzyme per g, the produced sugar was composed of 0.0% of glucose, 4.6% of maltose, 0.0% of maltotriose, 72.6% of maltotetraose, and 22.8% of other saccharides.

EXAMPLE 3

Starch was hydrolyzed by the use of the enzyme solution obtained in Example 1. As a substrate, 100 mg (as solid) of liquefied starch of DE 4.2 was used.

This substrate, with $5 \times 10^{-3}$M of calcium chloride and 2 units of the amylase G4 per g of substrate added in one lot and the same components plus 2 units and 5 units respectively of the pullulanase (produced by Nagase Biochemical Co., Ltd., Japan) produced by the microorganism of genus Klebsiella per g of the substrate added in other two lots, was made up with water to a total volume of 1 ml and incubated at 50° C. Samples of a fixed amount were taken from the reaction mixtures after 20 hours' and 44 hours' reaction and assayed for maltotetraose content by high-speed liquid chromatography. The results were as shown in Table 3.

TABLE 3

| Enzyme | | Maltotetraose content in hydrolyzate | |
|---|---|---|---|
| Amylase G4 | Pullulanase | 20 hours | 44 hours |
| 2 (u/g) | 0 (u/g) | 56.6 (%) | 64.6 (%) |
| 2 | 2 | 59.8 | 70.3 |
| 2 | 5 | 61.0 | 74.0 |

It is noted from the foregoing table that in the saccharification of starch by the use of amylase G4, when the reaction was carried out in the presence of pullulanase, it was accelerated so much as to give rise to a hydrolyzate having a higher maltotetraose content than when the amylase G4 was used alone.

EXAMPLE 4

As a substrate, 1 g (as solid) of liquefied potato starch of DE 4.2, with 4 units of the enzyme solution obtained in Example 1 and/or 500 units of barley β-amylase (produced by Böehringer Mannheium GmbH, with the activity determined by the method defined in "Agric. Biol. Chem., Vol. 40, pages 1515 (1976)) added in combination with $5 \times 10^{-3}$M of $CaCl_2$, was made up with water to a total volume of 10 ml and then incubated at pH 7 at 50° C. for 20 hours. After completion of the reaction, the resulting reaction solution was assayed for sugar composition by high-speed liquid chromatography. The results were as shown in Table 4.

TABLE 4

| Enzyme used | G1 (%) | G2 (%) | G3 (%) | G4 (%) | Others (%) |
|---|---|---|---|---|---|
| β-Amylase | 0.0 | 59.7 | 2.0 | 0.0 | 38.3 |
| Amylase G4 | 0.0 | 2.1 | 4.9 | 69.7 | 23.3 |
| β-Amylase + Amylase G4 | 0.0 | 72.4 | 6.5 | 0.0 | 21.1 |

(G1, G2, G3, and G4 stand respectively for monomer, dimer, trimer, and tetramer of glucose.)

EXAMPLE 5

Potato starch liquefied to a varying degree (DE) was used in a fixed amount of 1 g (as solid) as a substrate. The substrate with 10 units of the amylase G4, 1,000 units of barley β-amylase, and $5 \times 10^{-3}$M of $CaCl_2$ added, was made up with water to a total volume of 10 ml, and then incubated at 50° C. for 3 days. After completion of the reaction, the produced hydrolyzate was assayed for sugar content by high-speed liquid chromatography. The results were as shown in Table 5.

TABLE 5

| DE | G1 (%) | G2 (%) | G3 (%) | G4 (%) | Others (%) |
|---|---|---|---|---|---|
| 1.5 | 0.0 | 81.3 | 11.2 | 0.0 | 7.5 |
| 2.4 | 0.0 | 77.2 | 11.2 | 0.0 | 11.6 |
| 8.1 | 0.8 | 67.7 | 14.9 | 0.0 | 16.6 |

EXAMPLE 6

The procedure of Example 4 was repeated, except that 500 units of the β-amylase of Bacillus cereus var. mycoides (available from Hokkaido Sugat Co., Ltd., Japan) was used in place of the soybean β-amylase as a maltose-producing enzyme and the reaction was carried out at 50° C. for two days. The hydrolyzate consequently obtained was assayed for sugar composition. The results were as shown in Table 6.

TABLE 6

| | G1 | G2 | G3 | Others |
|---|---|---|---|---|
| Amylase G4 + Bacterial β-amylase | 0.0 | 74.9 | 7.0 | 18.1 |

What is claimed is:

1. A method for the production of a starch hydrolyzate rich in maltotetraose, which comprises:
   (i) aerobically culturing Bacillus circulans G-4 (FERM-BP 820) in a culture medium containing nitrogen sources and carbon sources at a pH of 5 to 9 and a temperature in the range of 20° to 60° C. to produce amylase G4 in said culture medium;
   (ii) collecting a solution consisting essentially of said amylase G4 from said culture medium;
   (iii) adding the collected amylase G4 to starch, amylopectin, glycogen or a partial hydrolyzate thereof to obtain a mixture; and
   (iv) subjecting said mixture to saccharification reaction conditions at a pH of 5 to 9 and a temperature in the range of 40° to 60° C.

2. The method of claim 1, wherein said saccharification reaction is carried out in the presence of α-1,6-glucosidase.

3. The method of claim 1, wherein said saccharification reaction is carried out in the presence of a calcium salt in a concentration of $5 \times 10^{-4}$ to $2 \times 10^{-2}$M.

4. A method for the production of a starch hydrolyzate rich in maltose, which comprises:
   (i) aerobically culturing Bacillus circulans G-4 (FERM-BP 820) in a culture medium containing nitrogen sources and carbon sources at a pH of 5 to 9 and a temperature in the range of 20° to 60° C. to produce amylase G4 in said culture medium;
   (ii) collecting a solution consisting essentially of said amylase G4 from said culture medium;
   (iii) adding β-amylase and the collected amylase G4 to starch to obtain a mixture; and
   (iv) subjecting said mixture to saccharification reaction conditions at a pH of 5 to 9 and a temperature in the range of 40° to 60° C.

* * * * *